United States Patent [19]

Boehringer

[11] 4,346,584
[45] Aug. 31, 1982

[54] GAS ANALYZER

[76] Inventor: John R. Boehringer, 427 Parkview Dr., Wynnewood, Pa. 19096

[21] Appl. No.: 199,110

[22] Filed: Oct. 20, 1980

[51] Int. Cl.³ ............................................. G01N 31/06
[52] U.S. Cl. ..................................... 73/23; 73/863.02; 73/861.75; 128/719
[58] Field of Search ........... 73/23, 19, 863.02, 861.74, 73/861.75; 128/719, 730

[56] References Cited

U.S. PATENT DOCUMENTS

| | | | |
|---|---|---|---|
| 1,685,557 | 9/1928 | Regelsberger | 128/719 |
| 3,530,714 | 9/1970 | Akeley | 73/861.75 |
| 3,910,261 | 10/1975 | Ragsdale et al. | 128/719 |
| 3,951,137 | 4/1976 | Conkle et al. | 128/719 |
| 4,202,352 | 5/1980 | Osborn | 128/719 |
| 4,233,842 | 11/1980 | Raemer et al. | 128/719 |

OTHER PUBLICATIONS

*Colorimetry and Gas Analysis*, Chapter 16, pp. 480–483.

Primary Examiner—Stephen A. Kreitman
Attorney, Agent, or Firm—Ratner & Prestia

[57] ABSTRACT

Apparatus for automatically analyzing a gas sample to determine the concentration of an absorbable gas therein, such as carbon dioxide in a patient's out breath. In the preferred embodiment, the end tidal volume of the patient's out breath is automatically sampled, drawn into a sample cylinder, circulated through an absorber, and the volumetric reduction effected by the absorption of the absorbable gas measured by a pressure indicator, all of which is cycled by the normal respiration cycle of the patient through an end of breath detector mechanism. The end of breath detector mechanism may also be used as a gas flow meter generally.

25 Claims, 7 Drawing Figures

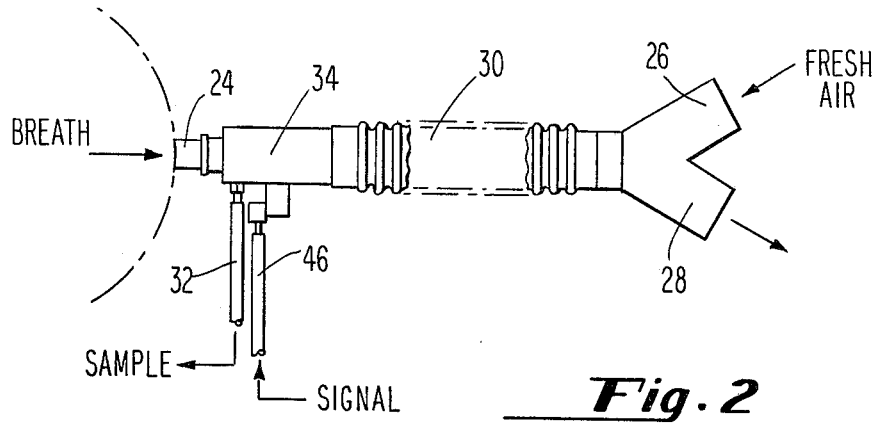
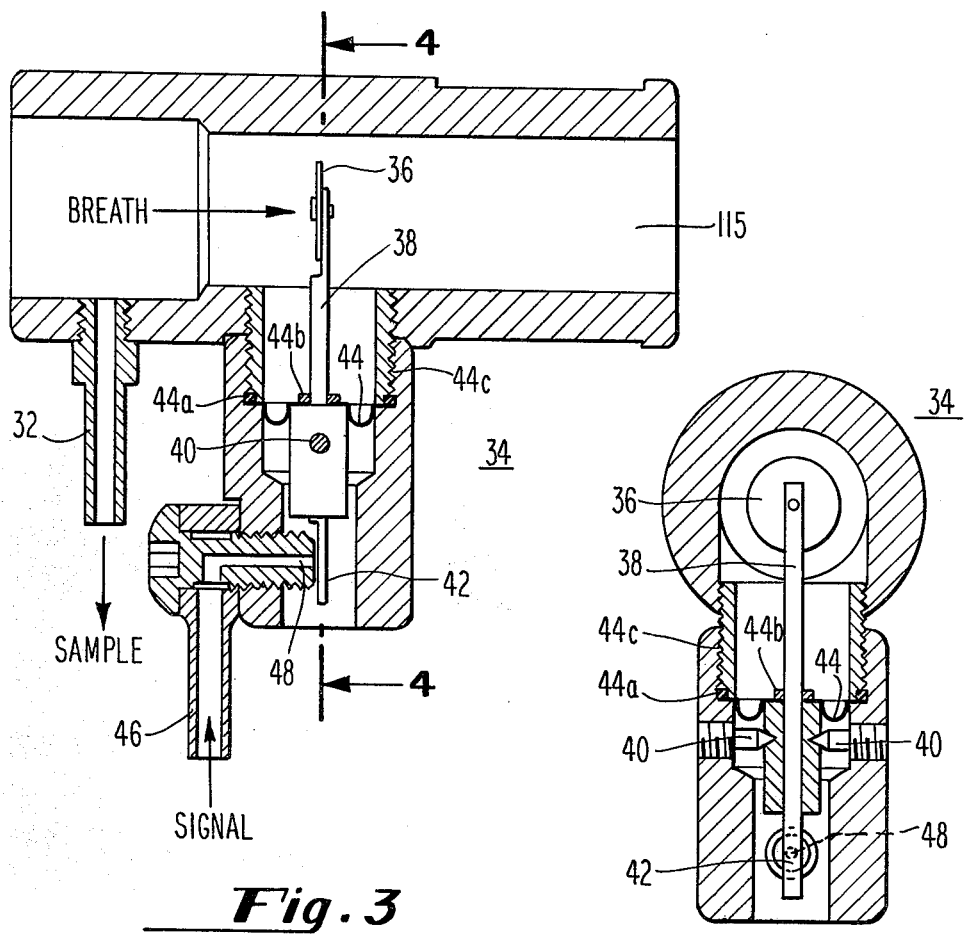
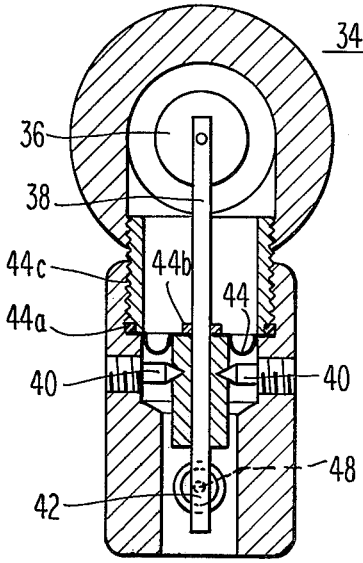

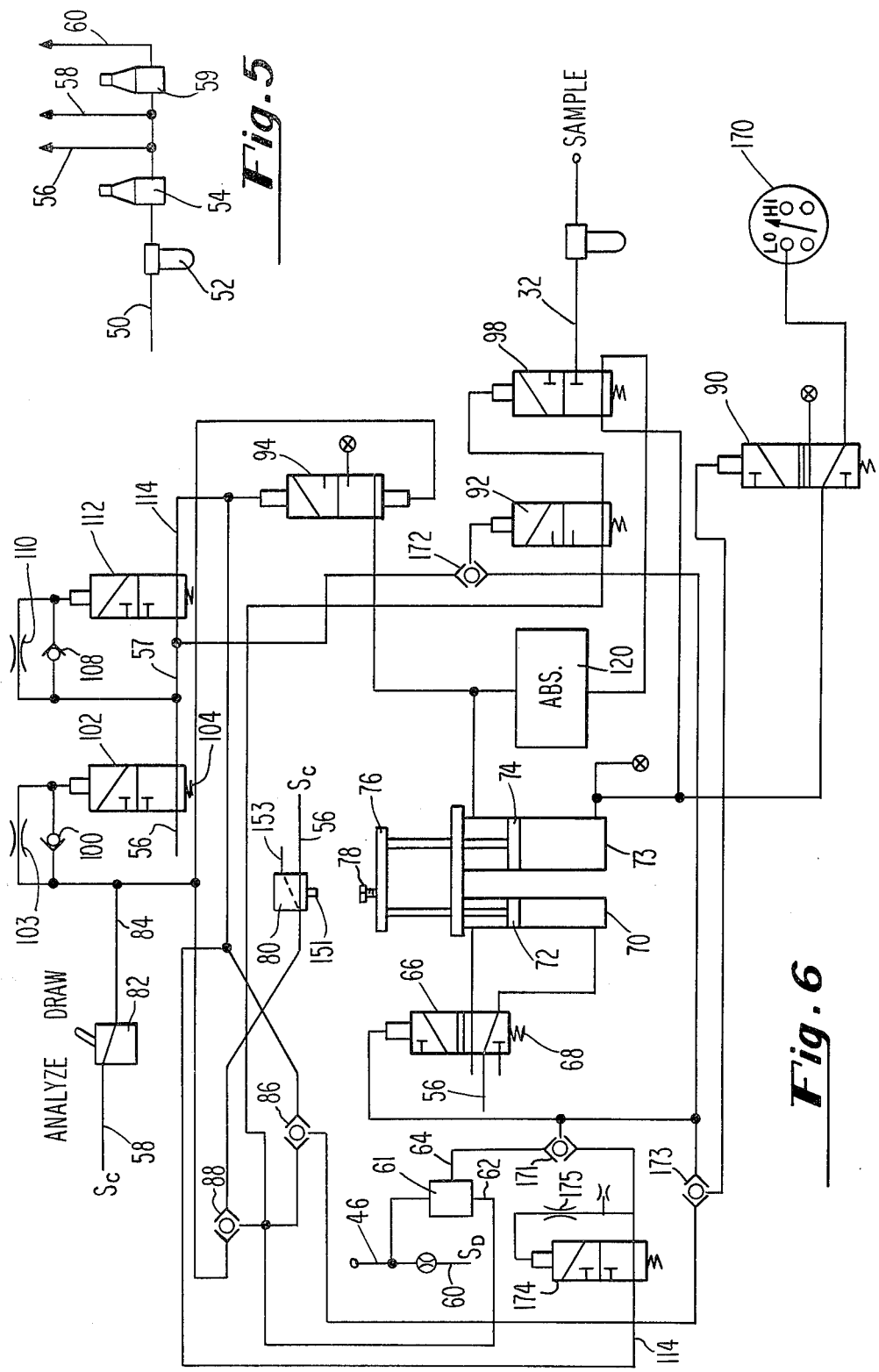

GAS ANALYZER

This invention pertains to an automatic gas analyzer based on selective absorption. (As used herein, the word "absorb" and its derivatives are intended also to encompass "adsorb" and its derivatives.) The preferred embodiment of the invention shown and described herein is particularly adapted to test for the carbon dioxide content in the end of exhalation or end tidal volume of an animal or human patient. End tidal gas concentration is becoming accepted as the best non-invasive technique for inference of arterial blood gas concentrations, thus avoiding the risk of arterial invasion.

In its most preferred form, this invention pertains to a pneumatic device suitable for connection in the respiratory or anesthetic breathing circuit of a patient whose end tidal volume $CO_2$ content is to be determined.

Batch and non-automatic processes for determination of carbon dioxide content in a sample gas, based upon absorption of $CO_2$ and volumetric reduction of the sample, are well known. "Orsat" apparatus for thus determining $O_2$, CO and $CO_2$ content in the stack gases of combustion equipment has been used for many years. Typically, the gas absorption process in the past has been carried out over water and the volumetric reduction measured by way of measuring liquid displacement by the sample gas before and after absorption. One automated form of such an analyzer is shown in the publication in *Colorimetry and Gas Analysis,* Chapter 16, Pages 480–483.

A similar, though non-automated, process has been adapted commercially for determination, by manual manipulation in a liquid system, of $CO_2$ content for physiological measurement in an animal or human patient exhalation. This process, as well as the system in which it is used, however, is cumbersome, lacks consistent and reliable accuracy, and does not perform automatically. Nor does it automatically provide for the taking of the sample from the end tidal volume of the patient, as is preferred. Moreover, because this process utilizes a liquid absorption medium, it is not capable of functioning in the presence of $N_2O$, halothane, and other organic agents normally found in the anesthetic circuit.

Other means now used for $CO_2$ determination in a breathing circuit include use of infrared absorption analyzers, or removal of a sample to a remote laboratory and standard electrode measurement; in extreme circumstances, mass spectrographic analyzation equipment may be used at or near the respiratory or operating room breathing circuit of the patient, from whom the analysis is being made.

All of these "secondary effect" instruments suffer from the need to perform a tedious daily calibration procedure with expensive calibration gas standards. In addition, the electronic systems suffer from inherent tendency to drift as optical and electronic components age.

The volumetric absorption system of this invention does not change calibration since the volume of sample is fixed mechanically during original manufacture and will not drift.

The infrared and mass spectroscopic systems are also very expensive in the accuracy ranges achieved by the absorption system described here. Automatic gas sampling and testing apparatus of the type disclosed in the present invention, and particularly including automatic end tidal volume sampling and measurement, has not heretofore been known insofar as the inventor herein is aware.

With this background, it is the general object of the present invention to provide a relatively simple and very accurate automatic apparatus for determining the partial pressure or concentration of an absorbable or adsorbable gas, such as $CO_2$, in a stream thereof.

It is a particular object of the present invention to provide a non-electronic and automatically functioning gas sampling and testing apparatus, including, in the preferred embodiment, an end of breath detector, and end tidal volume sample system, a respiration activated cycling system and a gas sampler and absorber-volumetric reduction measuring device, all adapted to function together in a compact and reliable manner, in line and convenient to a patient's respiratory or anesthetic breathing circuit for $CO_2$ measurement in the end tidal volume of the patient's exhalation. It is a further object to provide such a system which is unaffected by the usual ambient conditions of water vapor and the common anesthetic gases.

Most particularly, it is a primary object of this invention to make extremely fast and accurate determinations of blood gas levels available to the anesthesiologist during an operative procedure, on a less expensive and more reliable instrument, than is presently available.

These and other objects are met, in accordance with the present invention, by a system in which, in its preferred embodiments, the flowing gas to be sampled and tested also drives a sampling system and sampled gas cycling system. In accordance with the invention in its most general application, a measured volume of an automatically sampled gas is passed also automatically, through a closed circuit including an absorbent. Preferably, a partial pressure sensor for the absorbed gas in the closed circuit is automatically zeroed before sample cycling.

In the preferred form of the invention, which is adapted for end of breath $CO_2$ analysis, the cessation of flow at the end of an exhalation is used to signal or cycle a system to draw a sample (actually a sequence of such samples, so as to flush the system) from a downstream dead space tube, comprising the end tidal volume of a patient's exhalation, draw the sample into a sample cylinder of predetermined volume and, upon subsequent switching of the system to the "Analyze" mode (from the "Sample" mode) to initiate a timed delay to seal the gas sample into a test loop and during which system pressure equilibrates to ambient, and to circulate the gas in the sample cylinder through an absorber, until the absorbable gas (typically carbon dioxide) is removed. Thereafter, the volumetric reduction in the system is indicated by a pressure gauge, first having been zeroed at the beginning of the cycling sequence, and of which the volume change indication (actually a negative pressure increment from the "0" point) causes little system pressure change.

Preferably, this invention embodies a pneumatic system wherein pneumatic relays and gas pressure actuated valves are utilized to accomplish the foregoing functions, although other embodiments can readily be visualized using hybrid electrical-pneumatic or all electrical circuits, timers and pumps to sense and actuate the system.

For a better understanding of the present invention, reference may be made to the detailed description thereof which follows, taken in conjunction with the sub-joined claims and the accompanying drawings, in which:

DETAILED DESCRIPTION OF THE DRAWINGS

FIG. 2 is a schematic view of the preferred sampling mechanism in one form of the present invention;

FIG. 3 is a cross-sectional expanded view of a part of the sampling mechanism shown in FIG. 2, showing in detail the end of breath detector incorporated in this sampling mechanism;

FIG. 4 is a detailed cross-sectional view of the end of breath detector shown in FIG. 3, this sectional view taken in the plane 4—4 of FIG. 3;

FIG. 5 is a schematic illustration of the air supply system used in the pneumatically controlled gas analyzer of the preferred embodiment of the present invention;

FIG. 6 is a schematic view of the pneumatically controlled gas analyzer of the present invention in its preferred embodiment.

DETAILED DESCRIPTION OF THE PREFERRED EMBODIMENT OF THE INVENTION

Figure 1:
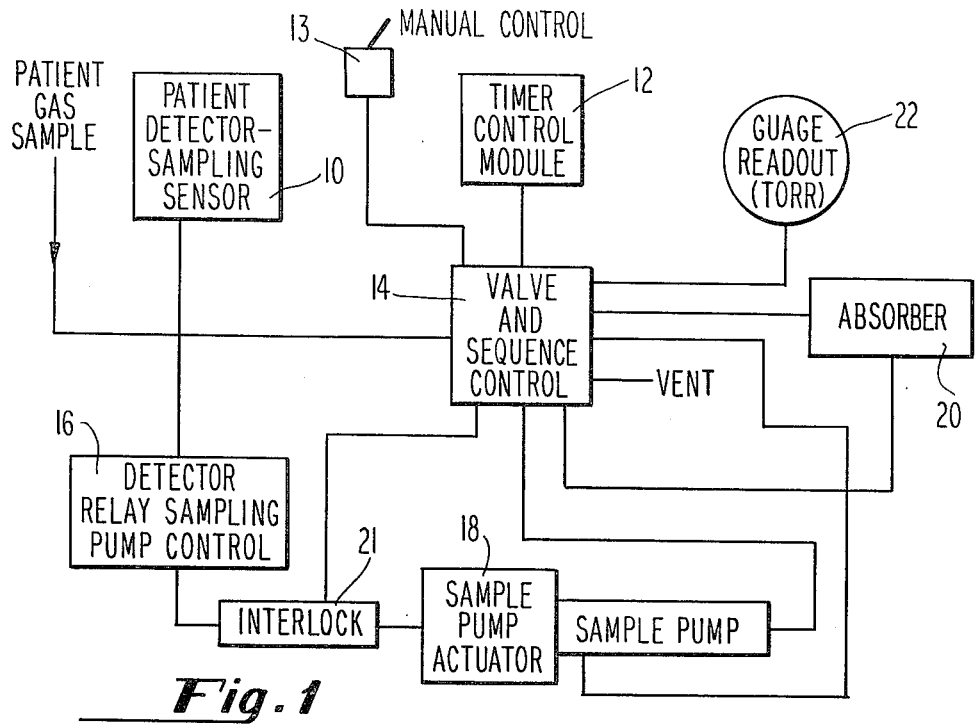
FIG. 1 is a block diagram illustrative of functional parts of the gas analyzer in the preferred form of the present invention.

More specifically, FIG. 1 illustrates, in block diagram form, an end tidal volume breath analyzer, including as functional components thereof, a patient detector-samping sensor 10, a timer control module 12, valve and sequence controls 14, detector-relay sampling pump control 16, sample pump actuator 18, together with sample pump 19, absorber 20 and gauge read-out 22, all adapted generally to give an output negative pressure indication of volumetric change (reduction) in the sample. Interlock 21 is provided to prevent sample pump actuation when the analyzer is not in the sampling mode.

The patient detector sampling sensor 10 is disposed to receive a gas sample, such as the end tidal volume of a patient's breath or exhalation disposed in the dead space of tube through which a patient is connected to a respirator. Patient detector sampling sensor 10 also includes means for indicating the end of exhalation or outbreathing so as to signal for the taking of an end tidal volume sample and also so as to signal for actuation of other parts of the system, specifically detector relay sampling pump control 16.

Timer control module 12 includes a manual selector switch 13 for switching the system from the sampling mode to the analyzing mode and for signaling, with appropriate time delays, the activation of selected valves and sequence controls in valve and sequence control 14. Valve and sequence control 14, at appropriate points in the functional sequence of the apparatus directs, through interlock 21, the gas sample to be analyzed to the sample pump actuator 18 and otherwise circulates gas sample from sample pump actuator 18 through pump 19 to absorber 20 and back to pump 19, while permitting gauge read-out 22 to indicate the volumetric change of gas in the absorber circuit, as an indication of the proportion of gas absorbed therein.

Detector relay sampling pump control 16 receives an "end of breath" signal from patient detector sampling sensor 10 and actuates sample pump actuator 18 either to receive a sample gas therein (with the selector switch in the "sample" mode), or to reverse actuate sample pump actuator 18 (with the selector switch in the "analyze" mode) so as to force the received sample outward into the absorber circulation circuit.

In this the preferred form of the present invention, a gas analyzer system, as schematically illustrated in FIG. 1, is adapted to sense the carbon dioxide content in a measured quantity of the end tidal volume of a patient's exhalation utilizing a gas sampler, as illustrated in FIG. 2. More specifically, endotracheal tube 24, typically connected to a patient, not shown, is also connected through detector 34, and a dead space tube 30 to a "Y" piece comprising an inspiratory line 26 and an expiratory line 28 of a respirator or anesthetic breathing machine, not shown. Between endotracheal tube 24 and "Y" piece tubes 26 and 28, tube 30 provides a dead air space reservoir for the capture of expiratory gas from the patient at the end of the exhalation cycle in the normal breathing sequence. Connected to the patient end of tube 30 is detector 34 with sampler tube 32, between seen in FIGS. 3 and 4.

Detector 34, as seen in FIGS. 3 and 4, consists of deflector flag 36 connected to an armature 38, pivoted at adjustable pivot points 40, and an armature flat 42 for blocking nozzle 48. Circuit pressure and moisture in breath detector passageway 115 at deflector 36 is sealed by diaphragm 44 from ambient. Detector tube 46 is maintained at a constant signal or detector positive pressure by connection to a detector pressure supply (not shown in FIGS. 2-4) and by the closure of the end of the detector tube passageway 48 by detector air valve armature flat 42, so long as the patient is exhaling and deflector flag 36 is deflected outwardly (rightwardly in FIG. 2). When the rightward positive pressure on deflector flag 36 ceases, at the end of the exhalation part of the breathing cycle, the positive pressure in detector tube 46 is released past detector nozzle air valve armature flat 42 and the pressure in tube 46 drops, typically to 5 cm $H_2O$ (gauge), thus producing an output signal for cycling sample pump activator 18 through detector relay sampling pump control 16. Thus, in the "sample" mode, an end tidal volume sample is drawn through sampler tube 32 from the patient and from dead space or volume in tube 30.

Detector 34, or modifications thereof, may also find use in other applications, such as to automatically trigger an X-ray camera at a particular point in a patient's breathing cycle. Still further, the control pressure in detector tube 46 may be either positive or negative (e.g., a vacuum), and the output signal sensed as a pressure change in detector tube 46 may comprise a variable signal (e.g., a pressure indicator) indicative of the pressure or flow rate during inhalation or exhalation.

Used in this manner, detector 34 may also comprise a pressure gauge or flow meter useful generally in any application requiring non-invasive gas stream measurement.

In the preferred form of the present invention, in which the method and apparatus of this invention are adapted to sense carbon dioxide content in the end tidal volume or end expiration of a patient, a pneumatic system as shown in FIG. 6 is utilized. This system is provided with pressurized gas (oxygen in the preferred embodiment although some other compressed gas such as air or nitrogen could also be used) from a pressurized gas feed system as illustrated in FIG. 5. There, it is seen that pressurized gas, from a supply source, not shown, is fed through inlet line 50 through a first filter 52 and a first pressure reducer 54, from which power gas is supplied, preferably in the embodiment of the present invention specifically described herein at a pressure of about 53 pounds per square inch, through power gas pressure supply line 56. Supply pressurized gas is also supplied to a control gas supply draw off 58, at 53 pounds per square inch in the preferred embodiment of the present invention. Still further, pressurized gas is passed through a second pressure reducer 59 and pressure reduced to provide a detector gas supply through detector gas supply line 60 at a pressure (in the preferred embodiment of the present invention) of about 4.1 pounds per square inch.

As seen in FIG. 6, detector gas supply line 60 is in communication via an orifice with detector tube 46 and the upside of diaphragm valve 61, the lower end of which includes an inlet 62 and an outlet 64, from which pressure is exhausted, when the pressure in detector tube 46 drops (to 5 cm H$_2$O in the typical design), i.e., when, at the end of an exhalation, deflector flag 36 ceases to be deflected rightwardly (as seen in FIG. 2). Loss of pressure in line 64, in turn, releases pneumatic relay 66 upwardly, urged by the pressure of biasing spring 68 to place power gas supplied from power gas supply line 56 in communication with the lower end of sample pump actuator cylinder 70, thereby to actuate actuator pump piston 72 upwardly together with sample cylinder piston 74, connected to actuator piston 72 by yoke 76, including an adjustable stop member 78 and an end of stroke detector 80.

Adjustable stop member 78 is pre-set to determine the end of stroke of yoke 76, together with pistons 72 and 74. End of stroke detector 80 functions to interrupt communication between control supply line 56 and high pressure selector valve 88, when yoke 71 contacts end of stroke trigger 151. In the event pressure to valve 88 is manually cut off while yoke 76 and associated pistons 72 and 74 are mid-stroke, control pressure is provided to valve 88 and to pneumatic relays 61 and 66 and actuator cylinder 70 by end of stroke actuator 80. When end of the stroke actuator 80 is triggered, at the end of the stroke of yoke 71 and associated pistons 72 and 74, downstream pressure from end of stroke actuator 80 is vented through vent line 153.

At the inception of the next exhalation deflector flag 36 is again deflected rightwardly (in FIG. 2), the pressure in detector tube 46 is sealed by the leftward deflection of valve stopper 42, pressure in line 46 increases back to the pressure of detector pressure supply line 60, namely 4.1 p.s.i. in the preferred embodiment of the present invention, and diaphragm valve 61 provides communication between lines 62 and 64 thereby providing the downward pressure on pneumatic relay 66, which shifts against the influence of biasing spring 68 and places air supply line 56 in communication with the upside of cylinder 70, thereby to cause a downstroke of actuator piston 72 and associated sampler piston 74, until piston 72 bottoms.

Outlet vents, preferably with "sound mufflers" in sample pump actuator relay 66 vents or dumps gas expressed from the upside or downside, alternatively, of pump actuating cylinder 70 upon application of positive pressure through relay 66 to the opposite side of piston 72.

Thus, with each breathing cycle of the patient, actuator piston 72 is actuated downward to pump sample gas out of sample gas cylinder 73 and with the end of each exhalation, actuator pump piston 72 is actuated upward to draw sample gas into sampler cylinder 73.

Similarly, alternate pressurization and depressurization of diaphragm valve outlet line 64 at the end of each exhalation and the inception of each exhalation, pressurizes the upside of pneumatic relay 92 through pressure switch 171 and 172 so as to place sample relay 98 and sample tube 32 in communication with the downside of sample cylinder 73 (through pneumatic relay 98) at the end of each exhalation cycle and, in the depressurized mode, to place the downside of sample cylinder 73 in communication with a vent outlet of pneumatic relay 94 through the absorber 120. In this manner, a previous sample in sample cylinder 73 is expressed outwardly through a vent upon downward activation of piston 74 and prior to receiving a new sample through sample tube 32.

The gas analyzer system of this invention includes two basic operating modes chosen by manual selector switch 82 through which, in the sampling or sample receiving mode ("Sample," as illustrated in FIG. 6), control pressure 58 is applied to control pressure sampling supply circuit 84, and in turn, through bi-functional high pressure selector switches 86, 88, and 173 to pneumatic relay 90 associated with air pressure gauge 170 and to the downside of pneumatic relay 94. In this manner pneumatic relays 90 and 94 are activated to vent gauge 170 and sample cylinder 73 and to place in communication sampler tube 32, from which sample gas is received, and the downside of sample cylinder 73.

Sampling circuit pressure network 84 also supplies control pressure, during the sampling mode, to a pneumatic timer sub-circuit consisting of a unidirectional valve 100, and pneumatic relay 102, pressurized downwardly by pressure through unidirectional valve 100 against spring biasing member 104 and which, upon the venting of the remainder of the control air supply circuit when selector 82 is switched to the "Analyze" mode, permits the return of the pneumatic relay 102 to its rest position, upwardly, by the escape of pressurized air through porous plug resistor 103, at a rate preselected to effect an eight (approximately) second delay in the pressure release of pneumatic relay 102.

Prior to the timing out of the eight second resistor 103 and return of the pneumatic relay 102 to its biased or rest position, but after switching of selector 82 to the "Analyze" mode, thus venting sampling supply circuit 84 to zero pressure, analyzer control gas pressure circuit 114 is also at zero pressure (gauge). During this eight second interval, there is no upside pressure on pneumatic relay 90 and under the influence of its internal biasing spring, pneumatic relay 90 returns to its biased or rest position, such that gauge 170 is placed in communication with the recycling circuit of sample tube 73. During this time, the sample in the analysis loop is "zeroed" so as to establish the set point for the gauge relative to system internal pressures and independent of ambient changes and independent of respiratory or manually induced breathing circuit pressures.

After timing out of the eight second delay porous plug resistor 103, upside pressure on pneumatic relay 102 is vented and control gas pressure line 56 is placed in communication through the downstream connection 57 thereof with a second pneumatic timer subcircuit consisting of unidirectional valve 108 and a ten second delay porous plug resistor 110, associated with a second delay pneumatic relay 112.

During this ten second delay, line 114 supplies oscillator relay 174 with pressure actuating pump drive cylinder through 171 and 66. As pressure bleeds through resistor 175, relay 174 fires downward and vents pressure to relay 66 reversing the pump cylinder with each cycle.

Also during this ten second delay period, analyze circuit network 114 is pressurized thus again venting gauge 170 through pneumatic relays 86, 173 and 90 and closing the recycle circuit of sample cylinder 73. Pressurization of analyzing circuit network 114 also provides upside pressure on pneumatic relay 94 so as to interrupt the communication between the upside of supply cylinder 73 and the vent outlet of pneumatic relay 94. During this ten second delay period then the recycle circuit from the downside of sample cylinder 73 to the upside thereof through pneumatic relay 98 and absorber 120 is completely closed and approximately four gas absorption passes are completed to and fro through the closed recycle circuit.

Upon the timing out of the ten second delay through pressure escape through resistor 110, upside pressure at pneumatic relay 112 is vented to zero and the communication between control pressure through line 57 and analyzing circuit network 114 is interrupted, network 114 then being vented at pneumatic relay 112 and the pressure therein dropping to zero. This reopens the connection between relay 90 and the downside of sample cylinder 73 and permits pressure measurement by gauge 170, now indicative of a volumetric reduction effected by absorption of the absorbable gas, $CO_2$, in this embodiment, in absorber 120. Gauge 170 is selected to give an accurate pressure output reading for the slight negative pressure thus produced by absorption of $CO_2$ and is calibrated so that the volumetric change effected by deflection of the pressure-sensitive diaphragm of gauge 170 has little effect on the pressure of the circuit. Thus, with the apparatus switched to the "Analyze" mode, there is approximately a eight second delay while the gauge 170 is zeroed and thereafter a ten second delay, to provide about four pumping cycles, during which activation of actuator piston 72 forces a recycling of sample gas from the downside of cylinder 73 through recycle circuit including absorber 120 to the upside of cylinder 73. This cycle is repeated about four times before the timing out of the ten second delay of timer relay 112 and at that point gauge 170 is brought into the circuit to read the negative pressure therein. In the preferred embodiment of the present invention, absorber 120 comprises a 500 cc cylinder in which is contained about ½ liter of absorbent mixture, consisting of moisturized barium hydroxide, sodium hydroxide and lithium hydroxide. This mixture in this quantity is good typically for about six months' use of the system as described.

Sample gas from end tidal volume sample tube 32 is admitted through sample gas inlet relay 98 upon downward actuation of pneumatic relay 98 through depressurization activated by end of breath sensor 34 and diaphragm valve 61. When un-pressurized, i.e., during positive pressure leftwardly of deflector 36, relay 98 vents return gases from the recycle sample gas circuit through absorber 120 and relay 94. In the event selector switch 82 is switched from the "Sample" mode to the "Analyze" mode or vice versa, in the middle of sample pump actuation, the pump stroke is completed by virtue of pressurization from control pressure inlet line 56 through end of stroke detector 80 as previously described.

In operation, end of breath detector 34 and associated elements in patient detector sampling sensor 10 activate sampling pump control relay 66 and piston 72, in turn cycling piston 74 of sample cylinder 73. In the "Sample" mode, this draws sampled gas from the connector tube 32, representing the end tidal volume of the patient, in a volume predetermined by the setting of adjustment screw 78, with the upside of piston 74 being vented. In the "Analyze" mode, cycling of piston 74 circulates the sampled gas in sample cylinder 73 via sample gas recycle pneumatic relay 98 through gas absorber 120 to the upside of piston 74 and sample cylinder 73 and back.

During the draw sample mode the exhaust sample gas is routed back through the absorber. In this way, the anesthetic gases themselves are used to saturate the absorber and circuit tubing and head end of pump cylinder. Thus by encouraging absorption and adsorption of these gases on the active (absorbing medium) and passive circuit elements (tubing, cylinder, lubricant), the error resulting from absorption of gases other than $CO_2$ is minimized or eliminated.

Similarly, it is important that all pneumatic relays in the system be thoroughly cleansed of contaminants and residual manufacturing debris prior to installation in order to avoid error-contributing variables in the system. This is particularly true of pneumatic relays which are part of the sample gas receiving and recycle sample gas circuits.

Figure 7:
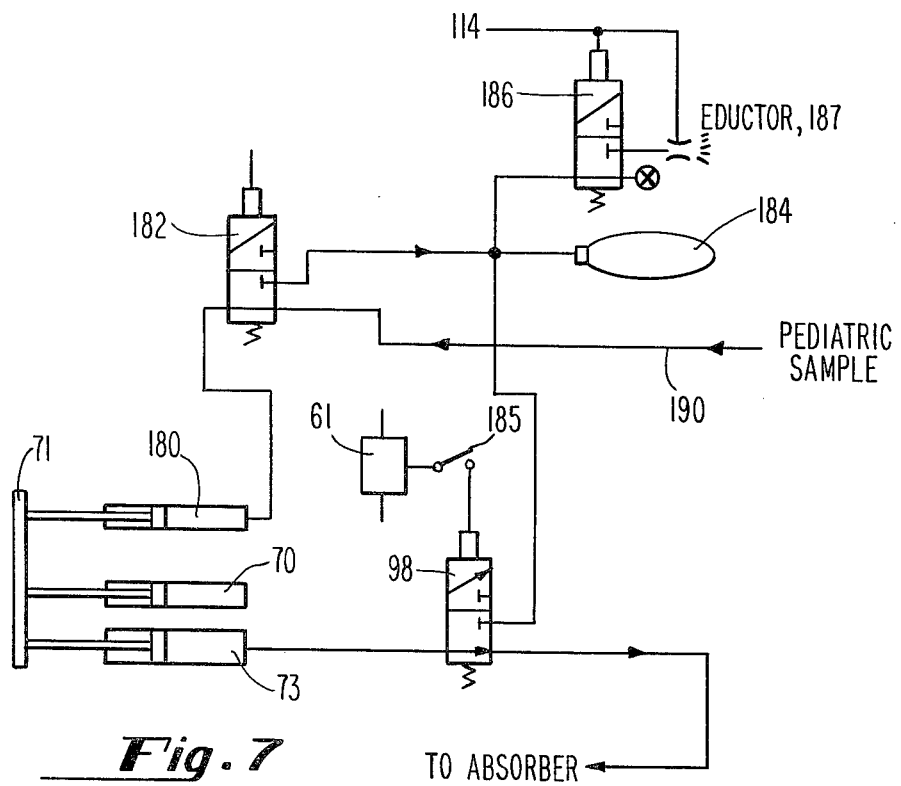
FIG. 7 is a schematic diagram of a modification of the system shown in FIG. 6, by which the system shown in FIG. 6 is specifically adapted for the testing of pediatric patients.

In the modification of the FIG. 6 gas analyzing system, shown in FIG. 7, the system is adapted for pediatric use by the addition of a third sampling cylinder 180, of substantially less volume than main sample cylinder 73, preferably on the order of 1/5 to 1/10 the volume of sample cylinder 73. In this embodiment of the invention, a second selector relay 182 is provided, along with a gas bag accumulator 184. An end tidal volume pediatric sample is passed from a sampling tube 190 into the pediatric special sample gas cylinder 180 via relay 182, and thence upon reverse stroke into gas bag accumulator 184. After, for example, twenty such cycles, sufficient gas sample is accumulated in gas bag accumulator 184 and selector switch 185 is switched to the "draw sample" position, such that in the next cycle, the accumulated gas sample in gas bag accumulator 184 is drawn into the main gas sample cylinder 73 from which point the system functions as previously described. A relay 186 and eductor 187 empty the bag of sample residual so that the next sample is not mixed with previous residual gas. (Other elements common to FIG. 6 are shown with like reference numerals.)

Typically, sample cylinder 73 is set to draw an end tidal volume on the order of 50 cubic centimeters and the gas accumulator bag 184 in the pediatric modification likewise has a typical volume on the order of 1000 cubic centimeters. The pediatric special sampling cylinder 180 typically has a volume on the order of about 10 cubic centimeters, and requires 20 cycles to fill gas accumulator bag 184.

For the pediatric system, or for high sensitivity adult versions of the embodiment of the invention otherwise disclosed and claimed herein, the end of breath detector, otherwise illustrated in FIG. 3, is also modified by the provision of an orifice or restrictor in breath detector passageway 115 just upstream of deflector 36 and sampler tube 32, so as to concentrate the kinetic energy of the relatively weaker pediatric or weak adult patient out-breath on deflector 36.

A critical factor in the end of breath detector component of the present invention is the free pivoting of deflector 36. For that purpose, adjustable needle pivot points 40 are provided, along with a minimum mass diaphragm 44, typically on the order of 0.005 inch thick silicone rubber, secured by integrally molded O-rings 44a and 44b and a threaded nipple fitting 44c.

In the preferred embodiment of the present invention, those elements referred to herein as pneumatic relays are typically commercially available two-way, three-way, and four-way pneumatic valves.

Possible variants of the present invention include:
(a) Use of a strain gauge as the output gauge mechanism such that the gauge output is an analog signal suitable for recording or, if converted to digital form, for digital read-out. This electric signal output in turn can then be used to drive high and low alarms and for computer logging;
(b) use of electronic or pneumatic-electronic relays instead of the pneumatic relays and timers in the embodiment disclosed;
(c) an end of breath sensor comprising a strain gauge, or an electro-optic sensor or an electronic (variable capacitance, variable reluctance, or variable resistance) sensor. The system may also include timers to hold or record a final output, readout, or signal and then automatically to initiate a new test sequence.

Still other possible variants include means for directing exhaust gases from the system over the sample cylinder to minimize deviations in the system output due to the temperature difference between the patient and ambient. Automatic adjustment of sample cylinder pump stroke may be provided to compensate for changes in ambient temperature and pressure.

In general, the gas analysis apparatus of this invention is believed useful in any application where it is desired to determine, quickly, reliably, and automatically, the concentration of a seletively absorbable gas in gas mixture streams.

While this invention has been described with reference to specific embodiments thereof, it is not limited thereto and the appended claims are intended to be construed to encompass not only those embodiments specifically referred to but also such other modifications and variants thereof as may be devised by those skilled in the art within the invention's true spirit and scope.

I claim:
1. Gas analyzer comprising:
(a) a volumetric gas sampling means comprising a gas receiving cylinder and piston;
(b) sampling means actuator for reciprocally driving said sampling means piston;
(c) means for triggering said actuator;
(d) valve means for selectively connecting said sampling means to a source of said sample gas, during the sample phase of operation of said analyzer, or to a closed recycle circuit including an absorber for a gas, the content of which in said sample gas is to be measured during the analyze phase of operation of said analyzer; and
(e) means for comparing the volume of sample gas in said recycle circuit before and after passage of said gas through said recycle circuit and absorber.

2. Gas analyzer, as recited in claim 1, wherein said means (c) comprises an end of breath sensor in a respiratory circuit signaling said actuator.

3. Gas analyzer, as recited in claim 1, wherein said actuator comprises a drive cylinder and piston, said drive piston connected to said sampling means piston to move in unison therewith.

4. Gas analyzer, as recited in claim 3, wherein said means (c) comprises an end of breath sensor in a respiratory circuit signaling said actuator.

5. Gas analyzer, as recited in claim 4, wherein said end of breath sensor comprises a deflector flag in a patient breathing tube adapted to connect a patient to a respiratory circuit and through which said patient's out breath is passed to said circuit, said deflector flag adapted to be deflected by said patient's out breath, said deflector flag being attached through a pivoted torque arm to a valve closure member adapted to signal an output pressure change in response to the deflection and deflection return of said deflector flag.

6. Gas analyzer, as recited in claim 5, wherein said source of said sample gas is a sample gas receiving tube located near said deflector flag in said patient breathing tube.

7. Gas analyzer, as recited in claim 4, further including a patient breathing tube adapted to connect a patient to a respiratory circuit and through which said patient's out breath is passed to said circuit, wherein said source of said sample gas is a sample gas receiving tube disposed near the patient end of said patient breathing tube adapted thereby to capture an end tidal volume sample.

8. Gas analyzer, as recited in claim 4, wherein said valve means (e) comprises a selector switching having two positions, in the first of which gas pressure source is operatively connected to a sample mode circuit including a pneumatic relay through which, upon activation of said actuator piston, sample gas is drawn into said sample gas cylinder on one side of the piston therein, and the other side of said sample cylinder is vented, and in the other of said position of said selector switch, gas pressure source is operatively connected to an analyze mode circuit including a pneumatic relay through which sample gas is circulated in said closed recycle circuit.

9. Gas analyzer, as recited in claim 1, wherein said volume comparing means is a pressure gauge adapted to indicate a relatively small increment of negative pressure in said recycle circuit and which is relatively insensitive to any pressure increment resulting from the volumetric change accompanying deformation of any pressure sensitive element in said gauge.

10. Gas analyzer, as recited in claim 8, wherein said volume comparing means is a pressure gauge adapted to indicate a relative small increment of negative pressure in said recycle circuit and which is relatively insensitive to any pressure increment resulting from the volumetric change accompanying deformation of any pressure sensitive element in said gauge.

11. Gas analyzer, as recited in claim 8, including a first delay means for delaying pressurization of said analyze mode circuit after said selector switch is switched from its first position to its second position and a venting means to vent said sample mode circuit pressure upon switching of said selector switch from its first position to its second position, said analyzer further including means for placing said pressure gauge in communication with said recycle circuit while both of said sample mode and analyze mode circuits are depressurized, and means for zeroing said pressure gauge while said delay means is operative.

12. Gas analyzer, as recited in claim 11, including a second delay means for automatically venting said analyze mode circuit a fixed period after pressurization thereof.

13. Gas analyzer, as recited in any of claims 1, 2, 7, 8 or 12, wherein said means (d) includes a pneumatic relay alternatively pressurized and depressurized from a signal controlled actuator activation power source to direct a pressurized pneumatic power supply connected through said relay to alternate sides of said actuator piston in said actuator cylinder, said activation power source being supplied alternatively from said sample mode circuit and said analyze mode circuit and, when both of said circuits are vented, by a third pressurization source connection, with means for interrupting said third pressurization source connection in response to a signal indicative of the end of the draw sample movement of said actuator piston and said sample piston, whereby said actuator piston completes its draw sample stroke notwithstanding the depressurization of said sample mode and analyze mode circuits during said draw sample stroke.

14. Gas analyzer, as recited in claim 3, 7 or 12, including a third cylinder and piston, said third piston also including means for unitary operation thereof with said first and second piston, said third piston adapted to receive a one breath pediatric sample, further including pediatric selector means whereby in the pediatric sample mode, the sample gas source is connected to said third cylinder, still further including a sample gas accumulator, with means for passing successive samples from said third cylinder into said accumulator and means, upon switching of said pediatric selector out of said pediatric sample mode, to draw the connected sample gas from said accumulator into said sample gas cylinder, whereby said accumulator functions as the sample gas source.

15. Gas analyzer, as recited in claim 14, including eductor means for automatically evacuating said accumulator during the analyze phase operation of said analyzer.

16. An analyzer as described in claim 1, wherein said means (c) includes an oscillator drive means to automatically cycle the instrument while in the analyze phase.

17. Gas analyzer, as recited in claim 1, including means for recycling sample gas from the previous sample phase cycle to said closed recycle circuit and to said absorber contained therein when said sample gas cylinder (a) is selectively connected to said sample gas source by said valve means (d), whereby the effect of non-absorbed gases in said sample gas are substantially nullified.

18. A detector as described in claim 16, utilizing a valve closure member adapted to signal an output pressure change in response to the deflection and deflection return of said deflector flag and a sample gas receiving tube located near said deflector flag in said patient's breathing tube.

19. Gas analyzer comprising:
   (a) means for automatically collecting a gas sample of a predetermined measured volume;
   (b) means for automatically passing said gas sample, after it has been collected, through an absorbent means for selectively absorbing a component of said gas sample;
   (c) means for automatically measuring the volumetric reduction in said gas sample after it has been treated by said selective absorption means, and for determining the concentration of said component in said sample as indicated by said volumetric reduction, wherein said collecting means comprises a sample receiving and holding chamber of predetermined volume, said chamber comprising a cylinder and reciprocable piston therein, the position of said piston and said cylinder dimensions, determining said predetermined volume.

20. Gas analyzer as recited in claim 19, wherein said collecting means is vented to ambient prior to activation of said automatic collecting means to eliminate the effect of sampling from a pressurized circuit.

21. Gas analyzer, as recited in claim 19, wherein said cylinder is selectively connected for connection to receive said sample and to pass said sample to a circuit including said absorbent means.

22. Gas analyzer, as recited in claim 21, wherein said piston is selectively actuable to draw said gas sample into said cylinder and to force said gas sample to said absorbent means circuit.

23. Gas analyzer, as recited in any of claims 20 to 22, wherein said concentration determining means comprises a pressure gauge, which is substantially insensitive to the volume change within the gauge at different pressures, and which is zeroed at the pressure and gas volume within the absorbent circuit, vented to ambient, prior to the introduction of said metered gas sample therein.

24. Gas analyzer, as recited in any of claims 20–22, particularly adapted to determine $CO_2$ concentration in an end-of-breath exhalation sample, including means for sensing the end of an exhalation cycle and for triggering said sample gas automatic collecting means to draw a sample of exhalation gases in response thereto.

25. Gas analyzer, as recited in claim 22, particularly adapted to determine $CO_2$ concentration in an end-of-breath exhalation sample, including means for sensing the end of an exhalation cycle and for triggering said sample gas automatically collecting means to draw a sample of exhalation gases in response thereto.

* * * * *